United States Patent [19]

Snyder et al.

[11] Patent Number: 5,212,061

[45] Date of Patent: * May 18, 1993

[54] DIRECT BINDING ASSAY FOR THE DETERMINATION OF A BACTEROIDES ORGANISM

[75] Inventors: Brian A. Snyder; Paul B. Contestable; Catherine T. Abrams, all of Rochester; Joseph J. Zambon, Amherst; Homer S. Reynolds, Tonawanda, all of N.Y.

[73] Assignee: Eastman Kodak Company, Rochester, N.Y.

[*] Notice: The portion of the term of this patent subsequent to Jul. 16, 2008 has been disclaimed.

[21] Appl. No.: 468,045

[22] Filed: Jan. 22, 1990

[51] Int. Cl.$^5$ ............... G01N 33/569; G01N 33/543
[52] U.S. Cl. .................... 435/7.32; 435/7.92; 435/7.95; 435/21; 435/28; 435/961; 435/962; 436/518; 436/531
[58] Field of Search ............ 435/7.32, 7.9, 7.92, 435/7.94, 7.95, 975, 968, 961; 436/518, 528, 529, 531, 534, 808; 422/68.1

[56] References Cited

U.S. PATENT DOCUMENTS 5,032,504  7/1991  Mauck .................... 435/7.36

FOREIGN PATENT DOCUMENTS 239776  10/1987  European Pat. Off. ........ 435/7.32
269388   1/1988  European Pat. Off. .

OTHER PUBLICATIONS

Zambon et al, "Immunological Assays for Putative Pathogens" Oral Microbiol. Immunol 1:39–44 (1986).
Nakazawa et al, "Serological Studies of Oral *Bacteroides intermedius*" Infect. Immun. 56(6): 1647–1651 (Jun. 1988).

Primary Examiner—Esther L. Kepplinger
Assistant Examiner—Carol E. Bidwell
Attorney, Agent, or Firm—J. Lanny Tucker

[57] ABSTRACT

Antigens extracted from one or more serotypes of a Bacteroides microorganism are rapidly and sensitively detected when directly bound to a water-insoluble substrate. The bound antigens are detected by forming an immunological complex on the substrate when the antigen reacts with the appropriate antibody. The antibody-antigen complex can be detected directly or by means of a second antibody which is directed to the Bacteroides antibody. The entire assay can be carried out at room temperature in less than about 15 minutes.

20 Claims, No Drawings

DIRECT BINDING ASSAY FOR THE DETERMINATION OF A BACTEROIDES ORGANISM

FIELD OF THE INVENTION

This invention relates to a direct binding method for the determination of a Bacteroides microorganism. This invention is useful in dental research and health care.

BACKGROUND OF THE INVENTION

There is a continuing need in medical, dental and veterinary practices, in research and diagnostic procedures, and for rapid and accurate detection or quantification of biological or chemical substances present in biological fluids or specimens. For example, the presence of various microorganisms in human and animal tissues, fluids or cells is very important for diagnosis and effective treatment of diseases.

Specific microorganisms have been implicated as markers for a number of periodontal diseases in humans and animals, such as gingivitis and periodontitis. The importance of such diseases is growing in the human population, especially as people live longer, and prevention thereof is becoming of considerable medical and commercial importance. In addition, the proper care of animals (including dental care) is a growing concern in our culture.

Detection of microorganisms associated with periodontal diseases has been accomplished using culture techniques (which are generally slow), DNA probes and a number of immunological procedures, such as agglutination assays, enzyme linked immunosorbent assays (ELISA), immunofluorescence and immunoprecipitation. The immunological procedures use immunological reactions of an antigenic site of the microorganism (which may be on a component extracted therefrom) with a corresponding antibody specific thereto. The resulting immunological reaction complex can then be detected in a number of ways.

The black-pigmented Bacteroides species are gram negative, anaerobic rods which are common in the etiology of various periodontal diseases, odontogenic abscesses and endodontic lesions. Such species include *Bacteroides intermedius, Bacteroides(Porphyromonas) gingivalis, Bacteroides forsythus* and *Bacteroides endodontalis. Bacteroides gingivalis* was recently renamed as *Porphyromonas gingivalis*. As defined herein, periodontal disease refers to a wide variety of diseases in humans and animals which occur in the periodontal area of the oral cavity, and includes diseases affecting the cemental surfaces of the roots of teeth, alveolar bone and the gingiva. It includes diseases that may occur at different times of human life, such as in infancy, youth, pregnancy or old age.

It is also known that certain serogroups or serotypes within a bacterial species which causes periodontal disease are responsible for certain forms of those diseases. For example, it is believed by some [Nakazawa et al, *Infect. Immun.*, 56(6), pp. 1647-1651, 1988] that serotype B of *Bacteroides intermedius* is responsible for human adolescent periodontitis, while serotypes B and C are responsible for adult periodontitis.

Clinical assays specific to such bacteria in gingival crevicular fluid and subgingival dental plaque are useful in the diagnosis of periodontal disease, in evaluating the options for and the progress of periodontal treatment, and in determining the status of the patient at later dental examinations. The standard culture techniques used to identify such organisms are time consuming, expensive and require a high level of operator expertise. Such tests also may lack sufficient sensitivity for detection of low levels of organisms due to strict anaerobic conditions required during transport.

The various immunoassays noted above have been developed and used with some success. Particularly useful are radioimmunoprecipitation assays and ELISA tests. U.S. Pat. No. 4,741,999 (issued May 3, 1988 to Genco et al) describes the production of monoclonal antibodies to antigens of *Actinobacillus actinomycetemcomitans* and their use in ELISA assays.

Monoclonal and polyclonal antibodies to various Bacteroides species have been prepared for similar assays [see for example Nakazawa et al, noted above and Zambon et al, *J. Periodon.*, 56(Supp), pp. 32-40, 1985].

Generally, the assays of the art have been slow, tedious and directed to a single organism. In many cases, the assays exhibit considerable cross-reactivity with related species, and thus have limited usefulness.

In copending U.S. Ser. No. 468,034 (filed on even date herewith by Snyder and entitled "Screening Assay for Microorganisms Associated with Periodontal Diseases, Article and Kit Useful Therein", now abandoned), a screening assay is described for detecting the presence of any of the three microorganisms *Actinobacillus actinomycetemcomitans, Bacteroides(Porphyromonas) gingivalis* and *Bacteroides intermedius*. This screening method is highly useful for practitioners so they can initially determine if a patient needs periodontal treatment.

However, once screening has been done, and the results are found to be positive, it would be desirable to be able to determine which microorganisms are present so the treatment can be prescribed specifically. Such treatment could then begin early. Presently, differentiation is carried out using the tedious culture or undesirable immunological methods described above.

Moreover, it would be useful to have an assay which is much more rapid, but as sensitive as known culture techniques.

SUMMARY OF THE INVENTION

The problems noted above with known analytical methods are overcome using a method for the determination of a Bacteroides microorganism comprising:

A. contacting a specimen suspected of containing at least one antigen extracted from a Bacteroides microorganism with a solid substrate for a sufficient time for the Bacteroides antigen to directly bind to the substrate, B. within about five minutes of the contacting, separating unbound materials from the bound Bacteroides antigen, and contacting the bound antigen with at least one antibody to the Bacteroides antigen to form an immunological complex bound to the substrate, and C. within about five minutes of the antibody-antigen contact, separating the bound complex from uncomplexed antibody and determining the presence of the bound complex as an indication of the presence of the Bacteroides antigen in the specimen.

The method of this invention is rapid, reliable and simple to use. For example, it can be carried out within about 15 minutes at room temperature. Thus, the tedious culture techniques and immunological assays known in the art are avoided. It is highly reliable for detecting an antigen extracted from a Bacteroides microorganism.

The present invention is carried out using a direct binding assay in which a simple solid substrate is used to "capture" extracted antigen. Antigen bound in this manner is contacted with the appropriate antibodies to form an immunological complex which can be readily detected.

For purposes of this invention, *Bacteroides gingivalis* is considered the same microorganism as *Porphyromonas gingivalis*, and is identified as *Bacteroides(Porphyromonas) gingivalis*.

DETAILED DESCRIPTION OF THE INVENTION

The present invention can be used to rapidly and sensitively detect antigens (for example, lipopolysaccharides, capsule antigens or membrane proteins) of a species of Bacteroides, for example antigens of any of *B. intermedius*, *Bacteroides(Porphyromonas) gingivalis*, *B. forsythus*, *B. endodontalis* and other species known to one skilled in the art. *B. intermedius* and *Bacteroides(Porphyromonas) gingivalis* are particularly detectable using the present invention. While the antigens may be detectable as part of intact cells, normally, they are extracted in a suitable manner from the whole cells present in a biological specimen. Such specimens include, but are not limited to, saliva or mucous from the throat or mouth, urine, lacrimal fluid, human or animal tissue extracts, dental plaque and gingival crevicular fluid. Generally, the organism is detected in dental plaque, saliva, or gingival crevicular fluid.

Antigen extraction is suitably accomplished using physical or chemical means, such as by use of detergents (such as sodium dodecyl sulfate, sodium deoxycholate or sodium decyl sulfate) using standard procedures, as described, for example, in U.S. Pat. No. 4,741,999 (noted above), osmotic shock [see for example, Dirienzo et al, *Infect. & Immun.*, 47(1), pp. 31-36, 1985], or sonic means [see for example, Zambon et al, *Infect. & Immun.*, 41(1), pp. 19-27, 1983].

Antibodies used in the practice of this invention can be monoclonal or polyclonal. Monoclonal antibodies can be prepared using standard procedures, such as those described in U.S. Pat. No. 4,741,999 (noted above). Polyclonal antibodies can also be produced using standard procedures, such as those described, for example in the Zambon et al reference noted above. Generally, a mammal (such as a rabbit) is immunized one or more times with a suitable quantity of antigenic component or whole bacterial cells of the organism. After a suitable time, when the titer is acceptable, antisera is recovered from the mammal. Antibodies can be removed from the antisera and purified if desired using known procedures and stored in frozen buffered solutions until used. They can be reactive with one or more serotypes of the same microorganism. Further details of such procedures are well known in the art. One method for providing highly specific polyclonal antibodies for specific serotypes of Bacteroides organisms is described in copending U.S. Ser. No. 468,393, filed on even date herewith by Reynolds et al and entitled "Bacteroides Polyclonal Antibodies and a Method for Their Preparation".

If desired, the antigenic material can be removed from the original specimen, or the original specimen can be suitably diluted with water or a suitable buffer, or filtered in order to remove extraneous matter and facilitate complexation of antigen and antibody in the assay.

Generally, once the antibodies are isolated, they can be stored and used in buffered solutions containing one or more suitable buffers and a preservative if desired. Preferably, they are stored in frozen form. In the buffered solutions, the pH is generally maintained at from about 6 to about 9, and preferably at from about 6.5 to about 8.5. Useful buffers include phosphate buffered saline solution, tris(hydroxymethyl)aminomethane, tricine, bicine, N-tris(hydroxymethyl)methyl-2-aminoethanesulfonic acid and others readily apparent to one skilled in the art.

Once antigen is extracted from the microorganism, it may be desirable in some instances, that the specimen be prefiltered to remove cellular debris or other potentially interfering materials. Prefiltering can be carried out using a suitable filtration device.

Extracted antigen is contacted with a suitable solid substrate to which the antigen can become bound quickly. Useful materials include those prepared from polymers, glass, ceramics, cellulosic materials and others known to one skilled in the art. The substrate can be configured in any desired shape or form, such as beads, films, porous membranes, gels or pellets. Polymeric materials are particularly useful, and can be used after a pretreatment or coating with materials which enhance antigen binding, or used without such pretreatments or coatings.

Preferred solid substrates are polymeric microporous membranes having an average pore size of from about 1 to about 10 $\mu$meter, and preferably an average pore size of about 5 $\mu$meter. Such membranes can be prepared from a variety of polymeric materials which can be fashioned into a thin membrane having the desired porosity, such as polyamides, polyesters, polyethyleneimines, polycarbonates, cellulosic materials and addition polymers prepared from ethylenically unsaturated polymerizable monomers.

In one embodiment, the polymeric substrate is positively charged, providing a positive zeta potential on the surface of the substrate. Zeta potential is known as the potential between the support and a fluid in contact with it, and is generally determined by measuring the voltage developed as the fluid is contacted with a support. Others techniques for measuring zeta potential are also known. Generally the cationic groups on such substrates are quaternary ammonium salts, quaternary phosphonium salts, quaternary sulfonium salts, quaternary pyridinium salts, quaternary pyrimidinium salts or quaternary imidazolium salts.

The charged substrate can be composed of a positively-charged polymer, or a composite of an uncharged polymer overcoated with a charged material. Examples of useful charged microporous membranes include, but are not limited to, the POSIDYNE ™ and BIODYNE ™ B microporous membranes (available from Pall Corp.).

Preferred microporous membranes are prepared from polyamides, that is, long chain synthetic polymers having recurring amide groups in the polymer backbone. Generally, polyamides are copolymers of a diamine and a dicarboxylic acid, or homopolymers of a lactam and an amino acid. Representative materials include, but are not limited to, polyhexamethylene dodecanediamide (nylon 612), polyhexamethylene adipamide (nylon 66), poly-$\epsilon$-caprolactam (nylon 6), polyhexamethylene sebacamide (nylon 610) and poly-7-aminoheptanoamide (nylon 7) and mixtures thereof. Further details of useful membranes and details of their preparation are found in U.S. Pat. No. 4,340,479 (issued Jul. 20, 1982 to Pall) and Pall Corp. trade literature brochures PSD-750a (March, 1983, pp. 1-20) and NM-900c (September, 1984, pp. 1-28). Preferred membranes are marketed by Pall Corp. as BIODYNE TM A and LOPRODYNE TM microporous membranes.

The substrates described above (and especially the microporous membranes) can be coated, if desired, with one or more surfactants in order to improve fluid flow and antigen binding. Various useful anionic, nonionic and amphoteric surfactants are described in *McCutcheon's Emulsifiers and Detergents*, 1986 Ed., McCutheon Division Publishing Co., Glen Rock, N.J., and include ZONYL TM FSN (DuPont), NONIDET TM P-40 (Sigma Chemical), and FLUOWET TM OT (American Hoechst).

The substrate described herein can be used in combination with other equipment in carrying out the assay (such as bottles, beakers, test tubes or cups). Alternatively and preferably, the substrate is a membrane which is mounted in a test device in which the assay is carried out and all fluids accommodated. Useful configurations of test devices are described, for example, in U.S. Pat. No. 3,825,410 (issued Jul. 23, 1974 to Bagshawe), U.S. Pat. No. 3,970,429 (issued Jul. 20, 1976 to Updike), U.S. Pat. No. 4,446,232 (issued May, 1984 to Liotta) and EP-A-0 308 231 (published Mar. 22, 1989) and EP-A-0 321 261 (published Jun. 21, 1989). The latter two references describe devices that are commercially available in SURECELL TM test kits (Eastman Kodak Company).

Most preferably, the test device contains a microporous membrane in each of three test wells, two test wells being for positive and negative controls. The extracted antigen is bound to the membranes in the test wells for immunological complexation with the appropriate antibodies. Such test devices have a water-insoluble shell into which the test wells are situated for convenient use. Embodiments other than those described in the art noted above would be readily apparent to one skilled in the art.

Almost immediately upon contact of the extracted antigen with the substrate, the antigen is directly bound thereto. By "directly" is meant that the antigen is not bound to the substrate through a linking moiety, or biological compound (such as an antibody) which is attached to the support. While some adsorption of antigen may occur, it is believed to be insignificant because the assay is carried out in insufficient time and under conditions not suitable for substantial adsorption. The antigen is preferably bound to the membrane as opposed to significant amounts of other materials, cellular components, whole blood or mucous which may be present in the test specimen.

Within about ten minutes, preferably within about one to about five minutes, and most preferably within about two minutes, of the contact of antigen with the substrate, the bound antigen is contacted with one or more antibodies directed thereto so as to form an immunological complex on the substrate. Fluid and unbound materials may be removed quickly at the same time, for example by drainage through a microporous membrane.

In one embodiment, the antibodies used to form the bound immunological complex on the substrate is labeled for detection of the complex. Useful labels are known in the art and include chemical and biological compounds which are directly detectable using suitable procedures and equipment, as well as compounds which can be detected through further chemical or specific binding reaction to provide a detectable species. Examples of useful labels include radioisotopes, enzymes, fluorescent compounds, chemiluminescent compounds, phosphorescent compounds, biotin or its derivatives, avidin or its derivatives, ferritin, magnetizable particles, dyes particles, gold sols, dye sols, colored *Staphylococcus aureus* cells and others readily apparent to one skilled in the art. Radioisotopes and enzymes are preferred labels. Labels are attached to antibody molecules using known techniques. Where the label is not directly detectable, further reagents or compounds are needed to render the reaction or specific binding product detectable. For example, if the label is biotin, a conjugate of biotin and an antibody can be reacted with avidin which is conjugated with a suitable enzyme. The appropriate substrate would be used to provide a detectable species from a resulting avidin-biotin specific binding complex. Where the label is an enzyme, such as glucose oxidase, peroxidase, urease, alkaline phosphatase or $\beta$-glucosidase, the appropriate substrates and dye-providing reagents are also needed.

In a particularly preferred embodiment, the label is peroxidase, and at some point in the assay hydrogen peroxide and suitable dye-providing reagents are added to provide a detectable dye in the presence of the immunological complex. Useful dye-providing reagents include, but are not limited to, triarylimidazole leuco dyes (such as those described in U.S. Pat. No. 4,089,747, issued May 16, 1978 to Bruschi).

In a preferred embodiment, a method for the determination of one or more serotypes of the microorganism *Bacteroides intermedius* comprises:

A. extracting at least one antigen from one or more serotypes of *Bacteroides intermedius* present in a biological specimen, B. contacting the extracted antigen with a solid substrate for a sufficient time for the extracted antigen to directly bind to the substrate, C. within about two minutes of the contacting, separating unbound materials from the bound antigen, and contacting the bound antigen with a labeled antibody to the antigen to form an immunological complex bound to the substrate, D. within about five minutes of the contacting in step C, separating the labeled bound complex from uncomplexed materials, and E. determining the labeled bound complex on the substrate as a measure of the amount of one or more serotypes of *Bacteroides intermedius* in the specimen.

This same method can be carried for the determination of one or more serotypes of *Bacteroides(Porphyromonas) gingivalis*.

In another embodiment of this invention, the a first antibody to the Bacteroides antigen is not labeled, and detection of the resulting bound immunological complex is accomplished using a second antibody (described below) which is specific to the unlabeled antibody and which is appropriately labeled.

Antibodies used in the method can be supplied in a composition which can contain various proteins and surfactants which reduce the nonspecific interactions on the substrate. Useful proteins include, but are not limited to, $\alpha$-casein, casein, fetal bovine serum and porcine gamma globulin. Useful surfactants include, but are not limited to, amphoteric surfactants such as those commercially available as LONZAINE ™ C amphoteric surfactants, and nonionic surfactants, such as those available as TWEEN ™ nonionic surfactants.

Once an immunological complex is formed on the substrate, incubation generally at room temperature (generally 18°–25° C.) for up to about five minutes is carried out. These are very mild incubation conditions compared to those used in the assay of other antigens by direct binding methods (see for example, U.S. Pat. No. 4,497,899).

After complex formation and incubation, the complex is washed one or more times to remove unbound materials. Generally, the wash solution has a pH of from about 7 to about 12 and contains one or more nonionic or cationic surfactants. A particularly useful wash solution includes a cationic surfactant (such as that sold as EMCOL ™ CC-9) in 3-(cyclohexylamino)-2-hydroxy-1-propanesulfonic acid buffer (pH 10).

In either of the embodiments described above where either one or two antibodies are used to form labeled complex bound to the substrate, the complex is directly or indirectly detected relatively quickly after washing the bound complex, that is generally within about ten minutes, and preferably within about one to about five minutes. If desired, detection can be hastened with incubation at a suitable temperature (such as room temperature) if the reagents warrant it.

The following examples are presented to illustrate, but not limit the scope of the invention. All percentages are by weight unless otherwise stated.

EXAMPLE 1

Direct Binding Assay for *Bacteroides Intermedius*

This example illustrates the practice of this invention to assay for all serotypes of *Bacteroides intermedius*.

Materials and Methods

SURECELL ™ test devices (Eastman Kodak Co.) were used containing 5 μm BIODYNE ™ A microporous membranes (Pall Corp.), coated with ZONYL ™ FSN nonionic surfactant (0.05 g/m$^2$, DuPont), in the three test wells.

A blocking composition comprised casein (0.5%) and merthiolate preservative (0.01%) in 3-(N-morpholino)-propanesulfonic acid (0.01 molar, pH 7.5).

Polyclonal antibodies directed against serotype A (ATCC 25611), serotype B (NCTC 9336) and serotype C (ATCC 49046) of *Bacteroides intermedius* were obtained by intravenous injection of white New Zealand rabbits using the procedure described in copending U.S. Ser. No. 468,393 of Reynolds et al (noted above). IgG fractions were prepared by ammonium sulfate precipitation and stored at 4° C. in phosphate buffered saline solution (0.03–0.04%). ATCC is the American Type Culture Collection (Rockville, Md.) and NCTC is the National Culture Type Collection (London).

The bacterial strains used to produce the antisera were supplied in viable cultures by Homer S. Reynolds (School of Dentistry, SUNY Buffalo). Isolates were subcultured as described in U.S. Ser. No. 468,393 of Reynolds et al (noted above).

Enzyme-antibody conjugates, directed against each serotype noted above, were prepared by covalently binding horseradish peroxidase to specific rabbit polyclonal antibodies by the procedure described by Yositake et al (*Eur. J. Biochem.*, 101, 395, 1979). The conjugate composition comprised each conjugate (5 μg/ml) in the blocking composition described above.

Antigens from the bacterial strains, corresponding to the serotypes noted above, were extracted using phosphate buffered saline solution (pH 7.3) for about one minute at room temperature.

The wash solution comprised EMCOL ™ CC-9 cationic surfactant (0.75%, Witco Corp.) and merthiolate (0.01%) in 3-(cyclohexylamino)-2-hydroxy-1-propane sulfonic acid (0.05 molar). The pH of the solution was raised to pH 10 by the addition of sodium hydroxide (0.05 Normal).

A dye-providing composition comprised 2-(4-hydroxy-3,5-dimethoxyphenyl)-4,5-bis(4-methoxyphenyl)imidazole (0.008%), poly(vinylpyrrolidone) (1%), sodium phosphate buffer (10 mmolar, pH 6.8), hydrogen peroxide (10 mmolar), 4'-hydroxyacetanilide electron transfer agent (2 mmolar) and diethylenetriaminepentaacetic acid chelating agent (10 μmolar).

Assay

The extracted antigen solutions (50 μl of each cell concentration) were added to two test wells of separate test devices and allowed to bind to the membranes in the test wells. Phosphate buffered saline solution (50 μl) was added to one test well of each device to provide negative controls.

The conjugate composition (50 μl) was added to each test well and the test devices were incubated at room temperature for five minutes. The wash solution (240 μl) was then added to the top of the resulting immunological complex in each test well twice, followed by addition of the dye-providing composition (50 μl). After incubation at room temperature for two minutes, the resulting dye formed on the membrane was visually evaluated and compared to a calibrated color chart of reflectance density values, then converted to transmittance density ($D_T$) using the Williams-Clapper transform (*J. Opt. Soc. Am.*, 43, 595, 1953).

The results of the assay, shown in Table I below, indicate that this invention can be used successfully to detect all three serotypes of *Bacteroides intermedius* using a direct binding assay. The background of the assay (0.011 $D_T$) was low, and the cell concentrations tested were determinable over it.

TABLE I

| Antigen Concentration (number of cells) | DT | | |
| --- | --- | --- | --- |
| | Serotype A | Serotype B | Serotype C |
| 6.3 × 10$^6$ | 0.215 | 0.101 | 0.175 |
| 7.8 × 10$^5$ | 0.114 | 0.042 | 0.101 |
| 2.0 × 10$^5$ | 0.057 | 0.019 | 0.027 |
| 0 (Control) | 0.011 | 0.011 | 0.011 |

EXAMPLE 2

Direct Binding Assay for *Bacteroides(Porphyromonas) Gingivalis*

This example illustrates the method of this invention to assay for all serotypes of *Bacteroides(Porphyromonas) gingivalis*.

The materials and methods used in this example were same as those for Example 1 except the polyclonal antibodies used herein were directed against serotype A (ATCC 33277), serotype B (ATCC 53978) and serotype C (ATCC 53977) of *Bacteroides(Porphyromonas) gingivalis*, and peroxidase-labeled conjugates were similarly prepared using these antibodies.

The assay was carried out using the procedure described in Example 1, and the results of the dye formation in the test devices are shown in Table II below. It is clear that this direct binding assay was useful to detect *Bacteroides(Porphyromonas) gingivalis* serotypes as the background is relatively low, and the dye density at all cell concentrations was determinable thereover.

TABLE II

| Antigen Concentration (number of cells) | DT | | |
|---|---|---|---|
| | Serotype A | Serotype B | Serotype C |
| $6.3 \times 10^6$ | 0.145 | 0.215 | 0.215 |
| $7.8 \times 10^5$ | 0.101 | 0.195 | 0.215 |
| $2.0 \times 10^5$ | 0.073 | 0.145 | 0.180 |
| 0 (Control) | 0.025 | 0.025 | 0.025 |

The invention has been described in detail with particular reference to preferred embodiments thereof, but it will be understood that variations and modifications can be effected within the spirit and scope of the invention.

We claim:

1. A method for the determination of a Bacteroides microorganism comprising:
   A. contacting at least one antigen extracted from a specimen suspected of containing a Bacteroides microorganism with a microporous membrane for a sufficient time for said Bacteroides antigen to directly bind to said membrane,
   B. within about five minutes of said contacting, separating unbound materials from said Bacteroides antigen bound to said membrane by washing said unbound materials through said membrane, and contacting said bound antigen with at least one antibody of said Bacteroides antigen to form an immunological complex bound to said membrane, and
   C. within about five minutes of contacting said antibody with said bound antigen, separating said bound immunological complex from uncomplexed antibody by washing said uncomplexed antibody through said membrane, and determining the presence of said bound complex on said membrane as an indication of the presence of said Bacteroides microorganism in said specimen,
   said method being carried out within about 15 minutes.

2. The method of claim 1 wherein said Bacteroides microorganism is *Bacteroides intermedius* or *Bacteroides (Porphyromonas) gingivalis*.

3. The method of claim 1 wherein said antibody is labeled with a radioisotope.

4. The method of claim 1 wherein said antibody is labeled with an enzyme, and complex determination is accomplished using a composition which provides a dye in the presence of said enzyme.

5. The method of claim 4 wherein said enzyme is peroxidase or alkaline phosphatase.

6. The method of claim 1 wherein said antibody is unlabeled, and after step B and before complex determination in step C, said complex is contacted with a labeled second antibody directed to said unlabeled antibody to form a detectable antigen-antibody-antibody immunological complex bound to said microporous membrane.

7. The method of claim 6 wherein said second antibody is labeled with an enzyme, and complex determination is accomplished using a composition which provides a dye in the presence of said enzyme.

8. The method of claim 1 wherein said microporous membrane is mounted in a disposable test device.

9. The method of claim 1 wherein said antibody is a polyclonal antibody directed to all serotypes of the Bacteroides microorganism being determined.

10. The method of claim 1 wherein multiple Bacteroides microorganisms are determined.

11. The method of claim 1 wherein said microporous membrane has an average pore size of from about 1 to about 10 μmeters.

12. The method of claim 11 wherein said microporous membrane is coated with a surfactant.

13. A method for the determination of one or more serotypes of the microorganisms *Bacteroides intermedius* comprising:
   A. extracting at least one antigen from one or more serotypes of *Bacteroides intermedius* present in a biological specimen,
   B. contacting said extracted antigen with a microporous membrane for a sufficient time for said extracted antigen to directly bind to said membrane,
   C. within about two minutes of said contacting, separating unbound materials from said bound antigen by washing said unbound materials through said membrane, and contacting said bound antigen with a labeled antibody to said antigen to form a labeled immunological complex bound to said membrane,
   D. within about five minutes of said contacting in step C, separating said labeled complex bound to said membrane from uncomplexed materials by washing said uncomplexed materials through said membrane, and
   E. determining said labeled bound complex on said membrane as a measure of the amount of one or more serotypes of *Bacteroides intermedius* in said specimen,
   said method being carried out within about 15 minutes.

14. The method of claim 13 wherein said antibody is labeled with peroxidase, and determination of said complex bound to said substrate is accomplished by contacting said complex with a composition comprising a leuco dye which provides a dye in the presence of peroxidase and hydrogen peroxide.

15. The method of claim 13 wherein said labeled antibody is polyclonal and specifically binds to two or more serotypes of *Bacteroides intermedius*.

16. The method of claim 13 wherein said labeled antibody is directed to a single serotype of *Bacteroides intermedius*.

17. A method for the determination of one or more serotypes of the microorganism *Bacteroides (Porphyromonas) gingivalis* comprising:
   A. extracting at least one antigen from one or more serotypes of *Bacteoides (Porphyromonas) gingivalis* present in a biological specimen,
   B. contacting said extracted antigen with a microporous membrane for a sufficient time for said extracted antigen to directly bind to said membrane,
   C. within about two minutes of said contacting, separating unbound materials from said antigen bound to said membrane by washing said unbound materials through said membrane, and contacting said bound antigen with a labeled antibody to said antigen to form an immunological complex bound to said membrane, D. within about five minutes of said contacting in step C, separating said labeled complex bound to said membrane from uncomplexed materials by washing said uncomplexed materials through said membrane, and E. determining said labeled complex bound to said membrane as a measure of the amount of one or more serotypes of *Bacteroides (Porphyromonas) gingivalis* in said specimen, said method being carried out within about 15 minutes.

18. The method of claim 17 wherein said antibody is labeled with peroxidase, and determination of said complex bound to said substrate is accomplished by contacting said complex with a composition comprising a leuco dye which provides a dye in the presence of peroxidase and hydrogen peroxide.

19. The method of claim 17 wherein said labeled antibody is polyclonal and specifically binds to two or more serotypes of *Bacteroides (Porphyromonas) gingivalis*.

20. The method of claim 17 wherein said labeled antibody is directed to a single serotype of *Bacteroides(-Porphyromonas) gingivalis*.

* * * * *